United States Patent
Hossainy et al.

(10) Patent No.: US 8,609,123 B2
(45) Date of Patent: Dec. 17, 2013

(54) DERIVATIZED POLY(ESTER AMIDE) AS A BIOBENEFICIAL COATING

(75) Inventors: Syed Faiyaz Ahmed Hossainy, Fremont, CA (US); Stephen Dirk Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1535 days.

(21) Appl. No.: 10/999,391

(22) Filed: Nov. 29, 2004

(65) Prior Publication Data

US 2006/0115513 A1   Jun. 1, 2006

(51) Int. Cl.
*A61K 38/44*    (2006.01)
*A61K 33/44*    (2006.01)
*A61K 31/727*   (2006.01)
*A61K 31/56*    (2006.01)
*A61K 31/573*   (2006.01)
*A61K 31/445*   (2006.01)
*A61K 31/4745*  (2006.01)
*A61K 31/337*   (2006.01)
*A61K 31/728*   (2006.01)

(52) U.S. Cl.
USPC .......................... 424/423; 424/94.4; 424/125

(58) Field of Classification Search
None
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et at. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,304,767 A | 12/1981 | Heller et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |
| 5,578,073 A | 11/1996 | Haimovich et al. |
| 5,581,387 A | 12/1996 | Cahill |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |

(Continued)

FOREIGN PATENT DOCUMENTS

DE   42 24 401    1/1994
EP   0 301 856    2/1989

(Continued)

OTHER PUBLICATIONS

OctoPlus Technologies May 16, 2004 web.archive.org/web/20041206221254/www/octoplus.nl/technologies/index.asp.*

(Continued)

*Primary Examiner* — Dennis Heyer (74) *Attorney, Agent, or Firm* — Squire Sanders (US) LLP (57) ABSTRACT

A derivatized poly(ester amide) (D-PEA) and coatings and medical devices formed therefrom are provided. The coatings and medical devices may optionally include a biobeneficial material and/or a biocompatible polymer and/or a bioactive agent. The medical devices can be implanted in a patient to treat, prevent, or ameliorate a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

23 Claims, 1 Drawing Sheet

(56) References Cited

U.S. PATENT DOCUMENTS

| | | | |
|---|---|---|---|
| 5,674,242 A | 10/1997 | Phan et al. | |
| 5,679,400 A | 10/1997 | Tuch | |
| 5,700,286 A | 12/1997 | Tartaglia et al. | |
| 5,702,754 A | 12/1997 | Zhong | |
| 5,711,958 A | 1/1998 | Cohn et al. | |
| 5,716,981 A | 2/1998 | Hunter et al. | |
| 5,721,131 A | 2/1998 | Rudolph et al. | |
| 5,723,219 A | 3/1998 | Kolluri et al. | |
| 5,735,897 A | 4/1998 | Buirge | |
| 5,746,998 A | 5/1998 | Torchilin et al. | |
| 5,759,205 A | 6/1998 | Valentini | |
| 5,776,184 A | 7/1998 | Tuch | |
| 5,783,657 A | 7/1998 | Pavlin et al. | |
| 5,788,979 A | 8/1998 | Alt et al. | |
| 5,800,392 A | 9/1998 | Racchini | |
| 5,820,917 A | 10/1998 | Tuch | |
| 5,824,048 A | 10/1998 | Tuch | |
| 5,824,049 A | 10/1998 | Ragheb et al. | |
| 5,830,178 A | 11/1998 | Jones et al. | |
| 5,837,008 A | 11/1998 | Berg et al. | |
| 5,837,313 A | 11/1998 | Ding et al. | |
| 5,849,859 A | 12/1998 | Acemoglu | |
| 5,851,508 A | 12/1998 | Greff et al. | |
| 5,854,376 A | 12/1998 | Higashi | |
| 5,858,746 A | 1/1999 | Hubbell et al. | |
| 5,861,387 A | 1/1999 | Labrie et al. | |
| 5,865,814 A | 2/1999 | Tuch | |
| 5,869,127 A | 2/1999 | Zhong | |
| 5,873,904 A | 2/1999 | Ragheb et al. | |
| 5,876,433 A | 3/1999 | Lunn | |
| 5,877,224 A | 3/1999 | Brocchini et al. | |
| 5,879,713 A | 3/1999 | Roth et al. | |
| 5,902,875 A | 5/1999 | Roby et al. | |
| 5,905,168 A | 5/1999 | Dos Santos et al. | |
| 5,910,564 A | 6/1999 | Gruning et al. | |
| 5,914,387 A | 6/1999 | Roby et al. | |
| 5,919,893 A | 7/1999 | Roby et al. | |
| 5,925,720 A | 7/1999 | Kataoka et al. | |
| 5,932,299 A | 8/1999 | Katoot | |
| 5,955,509 A | 9/1999 | Webber et al. | |
| 5,958,385 A | 9/1999 | Tondeur et al. | |
| 5,962,138 A | 10/1999 | Kolluri et al. | |
| 5,971,954 A | 10/1999 | Conway et al. | |
| 5,980,928 A | 11/1999 | Terry | |
| 5,980,972 A | 11/1999 | Ding | |
| 5,997,517 A | 12/1999 | Whitbourne | |
| 6,010,530 A | 1/2000 | Goicoechea | |
| 6,011,125 A | 1/2000 | Lohmeijer et al. | |
| 6,015,541 A | 1/2000 | Greff et al. | |
| 6,033,582 A | 3/2000 | Lee et al. | |
| 6,034,204 A | 3/2000 | Mohr et al. | |
| 6,042,875 A | 3/2000 | Ding et al. | |
| 6,051,576 A | 4/2000 | Ashton et al. | |
| 6,051,648 A | 4/2000 | Rhee et al. | |
| 6,054,553 A | 4/2000 | Groth et al. | |
| 6,056,993 A | 5/2000 | Leidner et al. | |
| 6,060,451 A | 5/2000 | DiMaio et al. | |
| 6,060,518 A | 5/2000 | Kabanov et al. | |
| 6,080,488 A | 6/2000 | Hostettler et al. | |
| 6,096,070 A | 8/2000 | Ragheb et al. | |
| 6,099,562 A | 8/2000 | Ding et al. | |
| 6,110,188 A | 8/2000 | Narciso, Jr. | |
| 6,110,483 A | 8/2000 | Whitbourne et al. | |
| 6,113,629 A | 9/2000 | Ken | |
| 6,120,491 A | 9/2000 | Kohn et al. | |
| 6,120,536 A | 9/2000 | Ding et al. | |
| 6,120,788 A | 9/2000 | Barrows | |
| 6,120,904 A | 9/2000 | Hostettler et al. | |
| 6,121,027 A | 9/2000 | Clapper et al. | |
| 6,129,761 A | 10/2000 | Hubbell | |
| 6,136,333 A | 10/2000 | Cohn et al. | |
| 6,143,354 A | 11/2000 | Koulik et al. | |
| 6,153,252 A | 11/2000 | Hossainy et al. | |
| 6,159,978 A | 12/2000 | Myers et al. | |
| 6,165,212 A | 12/2000 | Dereume et al. | |
| 6,172,167 B1 | 1/2001 | Stapert et al. | |
| 6,177,523 B1 | 1/2001 | Reich et al. | |
| 6,180,632 B1 | 1/2001 | Myers et al. | |
| 6,203,551 B1 | 3/2001 | Wu | |
| 6,211,249 B1 | 4/2001 | Cohn et al. | |
| 6,214,901 B1 | 4/2001 | Chudzik et al. | |
| 6,231,600 B1 | 5/2001 | Zhong | |
| 6,240,616 B1 | 6/2001 | Yan | |
| 6,245,753 B1 | 6/2001 | Byun et al. | |
| 6,245,760 B1 | 6/2001 | He et al. | |
| 6,248,129 B1 | 6/2001 | Froix | |
| 6,251,136 B1 | 6/2001 | Guruwaiya et al. | |
| 6,254,632 B1 | 7/2001 | Wu et al. | |
| 6,258,121 B1 | 7/2001 | Yang et al. | |
| 6,258,371 B1 * | 7/2001 | Koulik et al. | 424/422 |
| 6,262,034 B1 | 7/2001 | Mathiowitz et al. | |
| 6,270,788 B1 | 8/2001 | Koulik et al. | |
| 6,277,449 B1 | 8/2001 | Kolluri et al. | |
| 6,283,947 B1 | 9/2001 | Mirzaee | |
| 6,283,949 B1 | 9/2001 | Roorda | |
| 6,284,305 B1 | 9/2001 | Ding et al. | |
| 6,287,628 B1 | 9/2001 | Hossainy et al. | |
| 6,299,604 B1 | 10/2001 | Ragheb et al. | |
| 6,306,176 B1 | 10/2001 | Whitbourne | |
| 6,331,313 B1 | 12/2001 | Wong et al. | |
| 6,335,029 B1 | 1/2002 | Kamath et al. | |
| 6,344,035 B1 | 2/2002 | Chudzik et al. | |
| 6,346,110 B2 | 2/2002 | Wu | |
| 6,358,556 B1 | 3/2002 | Ding et al. | |
| 6,379,381 B1 | 4/2002 | Hossainy et al. | |
| 6,387,379 B1 | 5/2002 | Goldberg et al. | |
| 6,395,326 B1 | 5/2002 | Castro et al. | |
| 6,419,692 B1 | 7/2002 | Yang et al. | |
| 6,451,373 B1 | 9/2002 | Hossainy et al. | |
| 6,482,834 B2 | 11/2002 | Spada et al. | |
| 6,494,862 B1 | 12/2002 | Ray et al. | |
| 6,503,538 B1 | 1/2003 | Chu et al. | |
| 6,503,556 B2 | 1/2003 | Harish et al. | |
| 6,503,954 B1 | 1/2003 | Bhat et al. | |
| 6,506,437 B1 | 1/2003 | Harish et al. | |
| 6,524,347 B1 | 2/2003 | Myers et al. | |
| 6,527,801 B1 | 3/2003 | Dutta | |
| 6,527,863 B1 | 3/2003 | Pacetti et al. | |
| 6,528,526 B1 | 3/2003 | Myers et al. | |
| 6,530,950 B1 | 3/2003 | Alvarado et al. | |
| 6,530,951 B1 | 3/2003 | Bates et al. | |
| 6,540,776 B2 | 4/2003 | Sanders Millare et al. | |
| 6,544,223 B1 | 4/2003 | Kokish | |
| 6,544,543 B1 | 4/2003 | Mandrusov et al. | |
| 6,544,582 B1 | 4/2003 | Yoe | |
| 6,555,157 B1 | 4/2003 | Hossainy | |
| 6,558,733 B1 | 5/2003 | Hossainy et al. | |
| 6,565,659 B1 | 5/2003 | Pacetti et al. | |
| 6,572,644 B1 | 6/2003 | Moein | |
| 6,585,755 B2 | 7/2003 | Jackson et al. | |
| 6,585,765 B1 | 7/2003 | Hossainy et al. | |
| 6,585,926 B1 | 7/2003 | Mirzaee | |
| 6,605,154 B1 | 8/2003 | Villareal | |
| 6,616,765 B1 | 9/2003 | Hossaony et al. | |
| 6,623,448 B2 | 9/2003 | Slater | |
| 6,625,486 B2 | 9/2003 | Lundkvist et al. | |
| 6,645,135 B1 | 11/2003 | Bhat | |
| 6,645,195 B1 | 11/2003 | Bhat et al. | |
| 6,656,216 B1 | 12/2003 | Hossainy et al. | |
| 6,656,506 B1 | 12/2003 | Wu et al. | |
| 6,660,034 B1 | 12/2003 | Mandrusov et al. | |
| 6,663,662 B2 | 12/2003 | Pacetti et al. | |
| 6,663,880 B1 | 12/2003 | Roorda et al. | |
| 6,666,880 B1 | 12/2003 | Chiu et al. | |
| 6,673,154 B1 | 1/2004 | Pacetti et al. | |
| 6,673,385 B1 | 1/2004 | Ding et al. | |
| 6,689,099 B1 | 2/2004 | Mirzaee | |
| 6,695,920 B1 | 2/2004 | Pacetti et al. | |
| 6,706,013 B1 | 3/2004 | Bhat et al. | |
| 6,709,514 B1 | 3/2004 | Hossainy | |
| 6,712,845 B2 | 3/2004 | Hossainy | |
| 6,713,119 B2 | 3/2004 | Hossainy et al. | |
| 6,716,444 B1 | 4/2004 | Castro et al. | |
| 6,723,120 B2 | 4/2004 | Yan | |

(56) References Cited

U.S. PATENT DOCUMENTS

| | | |
|---|---|---|
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0049495 A1* | 4/2002 | Kutryk et al. ............ 623/1.47 |
| 2002/0051730 A1 | 5/2002 | Bodnar et al. |
| 2002/0065551 A1* | 5/2002 | Koole et al. ............ 623/1.25 |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0170685 A1* | 9/2004 | Carpenter et al. ............ 424/468 |
| 2005/0288481 A1* | 12/2005 | DesNoyer et al. ............ 528/310 |

FOREIGN PATENT DOCUMENTS

| | | |
|---|---|---|
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |

(56) References Cited

FOREIGN PATENT DOCUMENTS

| WO | WO 03/039612 | 5/2003 |
|----|----|----|
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2004/075781 | 9/2004 |

OTHER PUBLICATIONS

U.S. Appl. No. 10/630,250, filed Jul. 30, 2002, Pacetti et al.
U.S. Appl. No. 10/718,278, filed Nov. 19, 2003, Hossainy et al.
U.S. Appl. No. 10/719,516, filed Nov. 21, 2003, Tang et al.
U.S. Appl. No. 10/738,704, filed Dec. 16, 2003, Pacetti et al.
U.S. Appl. No. 10/741,214, filed Dec. 19, 2003, Pacetti et al.
U.S. Appl. No. 10/750,139, filed Dec. 30, 2003, Desnoyer et al.
U.S. Appl. No. 10/805,036, filed Mar. 16, 2004, Pacetti.
U.S. Appl. No. 10/816,072, filed Mar. 31, 2004, Dugan et al.
U.S. Appl. No. 10/835,656, filed Apr. 30, 2004, Tang et al.
U.S. Appl. No. 10/855,294, filed May 26, 2004, Pacetti et al.
U.S. Appl. No. 10/960,381, filed Oct. 6, 2004, Desnoyer et al.
U.S. Appl. No. 10/975,247, filed Oct. 27, 2004, Desnoyer et al.
U.S. Appl. No. 10/976,551, filed Oct. 29, 2004, Desnoyer et al.
Anonymous, *Cardiologists Draw-Up the Dream Stent*, Clinica 710:15 (Jun. 17, 1996), http://www.dialogweb.com/cgi/document?reg=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).
Anonymous, *Rolling Therapeutic Agent Loading Device for Therapeutic Agent Delivery or Coated Stent*(Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?ref=1061848017752, printed Aug. 25, 2003 (2 pages).
Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
Chung et al., *Inner core segment design for drug delivery control of thermo-responsive polymeric micelles*, Journal of Controlled Release 65:93-103 (2000).
De Lezo et al., *Intracoronary Ultrasound Assessment of Directional Coronary Atherectomy: Immediate and Follow-Up findings*, JACC vol. 21, No. 2, (1993) pp. 298-307.
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).
Matsumaru et al., *Embolic Materials for Endovascular Treatment of Cerebral Lesions*, J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Moreno et al., *Macrophage Infiltration Predicts Restenosis After Coronary Intervention in Patients with Unstable Angina*, Circulation, vol. 94, No. 12, (1996) pp. 3098-3102.
Nordrehaug et al., *A novel biocompatible coating applied to coronary stents*, EPO Heart Journal 14, p. 321 (p. 1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Oikawa et al., *Mechanisms of Acute Gain and Late Lumen Loss After Atherectomy in Different Preintervention Arterial Remodeling Patterns*, The Am. J. of Cardilogy, vol. 89, (2002) pp. 505-510.
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).
Peng et al., *Role of polymers in improving the results of stenting in coronary arteries*, Biomaterials 17:685-694 (1996).
Saotome, et al., *Novel Enzymatically Degradable Polymers Comprising α-Amino Acid, 1,2-Ethanediol, and Adipic Acid*, Chemistry Letters, pp. 21-24, (1991).
Scully et al., *Effect of a heparan sulphate with high affinity for antithrombin III upon inactivation of thrombin and coagulaton Factor Xa*, Biochem J. 262, (1989) pp. 651-658.
Shigeno, *Prevention of Cerebrovascular Spasm by Bosentan, Novel Endothelin Receptor*, Chemical Abstract 125:212307 (1996).
van Beusekom et al., *Coronary stent coatings*, Coronary Artery Disease 5(7):590-596 (Jul. 1994).
Virmani et al., *Lessons From Sudden Coronary Death a Comprehensive Morphological Classification Scheme for Atherosclerotic Lesions*, Arterioscler Thromb Vasc Biol. (2000) pp. 1262-1275.
Wilensky et al., *Methods and Devices for Local Drug Delivery in Coronary and Peripheral Arteries*, Trends Cardiovasc. Med. 3(5):163-170 (1993).
Yokoyama et al., *Characterization of physical entrapment and chemical conjugation of adriamycin in polymeric micelles and their design for in vivo delivery to a solid tumor*, Journal of Controlled Release 50:79-92 (1998).
International Search Report for PCT/US2005/042541 filed Nov. 21, 2005, mailed May 19, 2006, 10 pgs.
Dibutyl Sebacate, Product Identification, Chemical Land21.com, 2 pgs. Nov. 4, 2003.
Diederich "Covalent fullerene chemistry", Pure & Appl. Chem. vol. 69, No. 3, pp. 395-400 (1997).
Luo "Cross-linked hyaluronic acid hydrogel films". J. of Controlled Release 69, pp. 169-184 (2000).

(56) References Cited

OTHER PUBLICATIONS

Mehdipour-Ataei et al., "Synthesis, Characterization and properties of novel poly(ester-amide-urethane)s", Abstract, 3 pgs. Downloaded from: www.sun.ac.za/unesco/Conferences?Conference2003/ABSTRACT/MEHDIPOIUR.htm, Nov. 3, 2003.

Sang-II Han et al., "Cellular interactions and degradation of aliphatic poly(ester amide)s derived from glycine and/or 4-amino butyric acid", Biomaterials 24, pp. 3453-3462 (2003).

Yang "Design and synthesis of fullerne-based amino acids", Abstract 3 pgs (2004).

* cited by examiner

DERIVATIZED POLY(ESTER AMIDE) AS A BIOBENEFICIAL COATING

BACKGROUND OF THE INVENTION

1. Field of the Invention

This invention generally relates to a derivatized poly(ester amide) composition useful for coating an implantable device such as a drug delivery stent.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient. One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent surfaces a coating of the polymer and the therapeutic substance impregnated in the polymer.

Generally, a polymer forming a coating composition for an implantable device has to be biologically benign. The polymer is preferably biocompatible and bioabsorbable. One such polymer is poly(ester amide). Poly(ester amide) (PEA) has excellent biocompatibility. However, a coating formed of PEA can incur mechanical failures. In addition, PEA is more permeable to a drug such as everolimus than ethylene vinyl (EVAL) alcohol copolymer and polyvinylidene fluoride (Solef™). In order to achieve a proper level of residence time of an agent in a coated stent, it would require thicker coatings to meet release rate targets.

Therefore, there is a need for a PEA coating composition that provides for a controlled release of a bioactive agent and improved mechanical properties.

The compositions and the coatings formed thereof disclosed herein address the above described problems and needs.

SUMMARY OF THE INVENTION

An embodiment of the present invention provides a biobeneficial composition that contains a derivatized poly(ester amide) (D-PEA) for coating a medical device such as a stent or forming an implantable medical device itself such as a stent. The D-PEA contains a biobeneficial moiety. The implantable device or coating can optionally include a bioactive agent for controlled release of the agent. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and combinations thereof. The implantable device can be implanted in a patient to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

DETAILED DESCRIPTION

In one embodiment of the present invention, a biobeneficial composition is provided that contains a derivatized poly(ester amide) (D-PEA), optionally with another biocompatible polymer and/or a biobeneficial material, for coating a medical device such as a stent or forming the implantable medical device itself. The D-PEA contains a moiety derived from another biocompatible polymer or from a biobeneficial material. Preferably, the D-PEA contains a moiety derived from a biobeneficial material.

The implantable device or coating can optionally include a bioactive agent for controlled release of the agent. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and combinations thereof. The implantable device can be implanted in a patient to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

Poly(ester Amide) Polymers

Poly(ester amide) (PEA) is a class of polymer having both ester and amide functionalities in its backbone. It is generally formed of a diacid and another moiety having both amino and ester functionalities. One of such PEA is described in, e.g., U.S. Pat. No. 6,503,538, B1.

The diacid is preferably a C2-C12 diacid, aliphatic or with unsaturation. The amino acid can be, for example, glycine, valine, alanine, proline, glutamine, methionine, leucine, isoleucine, or phenylalanine. An optional second amino acid may be included. The second amino acid can be, for example, lysine, tyrosine, tryptophan, arginine, histidine, glutamic acid, aspartic acid, threonine, serine, or cysteine. The second amino acid may contain a side group to enable the attachment of pharmacologically active compounds or property modifi- ers. PEA polymers with various thermal properties can be readily prepared by varying these components during synthesis.

PEA can be made by condensation polymerization utilizing, among others, diamino subunits and dicarboxylic acids (Scheme I). In Scheme I, the dicarboxylic acids are converted to an active di-p-nitrophenyl derivative. As shown in Scheme I, when the dicarboxylic acid and the diamino subunits are used stoichiometrically, the PEA formed would have one terminal carboxylic acid group and one terminal amino group. When the dicarboxylic acid and the diamino subunits are not used at a ratio of 1:1, the PEA thus formed can have end groups in favor of the carboxylic acid group, if the dicarboxylic acid subunit is used more than the diamino subunit, or in favor of the amino group, if the diamino subunit is used more than the dicarboxylic acid subunit. Accordingly, the PEA molecule would have reactive carboxylic acid or amino end groups.

cantly below that of the biocompatible polymer, described below. In some embodiments, the $T_g$ is below human body temperature. This attribute would, for example, render the biobeneficial material relatively soft as compared to the biocompatible polymer and allows a layer of coating containing the biobeneficial material to fill any surface damages that may arise when an implantable device is coated with a layer comprising the biocompatible polymer. For example, during radial expansion of the stent, a more rigid biocompatible polymer can crack or have surface fractures. A softer biobeneficial material can fill in the crack and fractures.

Another attribute of a biobeneficial material is hydrophilicity. Hydrophilicity of the coating material would affect the drug release rate of a drug-delivery coating and, in the case that the coating material is biodegradable, would affect the degradation rate of the coating material. Generally, the higher hydrophilicity of the coating material, the higher the drug Scheme I

Biobeneficial Material

In one embodiment, the biobeneficial material can be used to derivatize a PEA polymer to form the derivatized PEA polymer (D-PEA) described herein, which is used to form a coating or an implantable device. In another embodiment, the biobeneficial material can be used in combination with the D-PEA to form a coating of an implantable device. The biobeneficial material can be a polymeric material or non-polymeric material. The biobeneficial material is preferably flexible and biocompatible and/or biodegradable (a term which includes bioerodable and bioabsorbable), more preferably non-toxic, non-antigenic and non-immunogenic. A biobeneficial material is one which enhances the biocompatibility of a device by being non-fouling, hemocompatible, actively non-thrombogenic, pro-endothelial cell proliferation, or anti-inflammatory, all without depending on the release of a pharmaceutically active agent.

Generally, the biobeneficial material has a relatively low glass transition temperature ($T_g$), e.g., a $T_g$ below or signifirelease rate of the drug-delivery coating and the higher the degradation rate of the coating if it is biodegradable.

Representative biobeneficial materials include, but are not limited to, polyethers such as poly(ethylene glycol) (PEG), copoly(ether-esters) (e.g. poly(ethylene oxide)/polylactide (PEO/PLA)); polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, and combinations thereof. In some embodiments, the polymer can exclude any one of the aforementioned polymers.

In an embodiment, the biobeneficial material is a block copolymer having flexible poly(ethylene glycol) and poly (butylene terephthalate) blocks (PEGT/PBT) (e.g., PolyActive™). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In further embodiment, the biobeneficial material can be poly(ethylene glycol), peptide ampihile, a nitric oxide preserver such as 4-amino-2,2,6,6-tetramethylpiperidine-N-oxyl (4-amino-TEMPO), pro-healing polymers such as NO-donor polymers, hyaluronic acid, carbon nanotubes, and fullerenes.

Biocompatible Polymer

The biocompatible polymer that can be used with the D-PEA described herein in the coatings or medical devices described herein can be any biocompatible polymer known in the art, which can be biodegradable or nondegradable. Representative examples of polymers that can be used to coat an implantable device in accordance with the present invention include, but are not limited to, poly(ester amide) that is not the D-PEA defined herein, ethylene vinyl alcohol copolymer (commonly known by the generic name EVOH or by the trade name EVAL), poly(hydroxyvalerate), poly(L-lactic acid), poly(L-lactide), poly(D,L-lactide), poly(L-lactide-co-D,L-lactide), polycaprolactone, poly(lactide-co-glycolide), poly (hydroxybutyrate), poly(hydroxybutyrate-co-valerate), polydioxanone, polyorthoester, polyanhydride, poly(glycolic acid), poly(D,L-lactic acid), poly(D,L-lactide-co-glycolide) (PDLLAGA), poly(glycolic acid-co-trimethylene carbonate), polyphosphoester, polyphosphoester urethane, poly (amino acids), polycyanoacrylates, poly(trimethylene carbonate), poly(iminocarbonate), poly(butylene terephthalate-co-PEG-terephthalate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as vinylidene fluoride based home or copolymer under the trade name Solefr™ or Kynar™, for example, polyvinylidene fluoride (PVDF) or poly(vinylidene-co-hexafluoropropylene) (PVDF-co-HFP) and polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

A preferred biocompatible polymer is poly(ester amide), poly(ortho esters), poly(anhydrides), poly(D,L-lactic acid), poly (L-lactic acid), poly(glycolic acid), copolymers of poly (lactic) and glycolic acid, poly(L-lactide), poly(D,L-lactide), poly(L-lactide-co-D,L-lactide), poly(L-lactide-co-glycolide), poly(D,L-lactide-co-glycolide), poly(phosphoesters), poly(trimethylene carbonate), poly(oxaesters), poly (oxaamides), poly(ethylene carbonate), poly(propylene carbonate), poly(phosphoesters), poly(phosphazenes), poly (tyrosine derived carbonates), poly(tyrosine derived arylates), poly(tyrosine derived iminocarbonates), copolymers thereof with poly(ethylene glycol), or combinations thereof.

Derivatization of Poly(ester Amide) Polymers

The PEA can be modified via the terminal carboxyl groups or amino groups. The following embodiments describe some exemplary methods of derivatizing a PEA polymer.

Derivatization via the Carboxylic Acid Group of the PEA Polymer

In some embodiments, a D-PEA can be formed via the carboxyl group of the PEA polymer by reacting the carboxyl group with a biobeneficial material having a functional group capable of reacting with the carboxyl group, as shown in Scheme 2. The functional group of the biobeneficial moiety can be any functional group capable of reacting with a carboxyl group. Such functional groups can be a reactive group or a leaving group, which include, but are not limited to, hydroxyl, thiol, amino, carboxyl, ester, keto, aldehyde, halide, tosylate, or mesylate.

Scheme 2

BM = biobeneficial moiety
X = functional group which is a reactive or a leaving group In scheme 2, the carboxyl on the PEA may also be an activated carboxyl such as a p-nitrophenyl derivative, acid halide, or N-hydroxysuccinimidyl derivative.

In one embodiment, the biobeneficial material has a carboxyl group and can be coupled to a PEA polymer via carboxyl-carboxyl coupling. This coupling can be mediated by, for example, a water soluble carbodiimide such as (1-ethyl-3-(3-(dimethylamino)propyl)carbodiimide (EDC), or an organic soluble carbodiimide such as dicyclohexylcarbodiimide to yield an anhydride linkage.

Amine terminated biobeneficial material can be directly coupled to carboxylic acid moieties using an agent such as a carbodiimide, specifically EDC mediated by an agent such as N-hydroxybenzotriazole (HOBT), substituted HOBT, or N-hydroxysuccinamide.

Derivatization via Hydrazide

In another aspect of the present invention, a PEA polymer having carboxyl groups on its backbone can be coupled to a hydrazide reactive group in an aqueous medium such as water. A linking agent with at least two hydrazide reactive groups would be capable of coupling the PEA polymer with a biobeneficial material having carboxylic acid groups. In order to avoid crosslinking of a biobeneficial material bearing multiple carboxylic acid groups by the linking agent, the reaction can be done in an excess of the linking agent such as a dihydrazide, and the degree of functionalization can be controlled by the amount of a carbodiimide such as EDC (Scheme 3) (Luo, Y. et al., J. Contr. Release 69:169-184 (2000)).

Scheme 3

The functionalized PEA, which has a remaining hydrazide group, can react with the carboxylic acid residue on the biobeneficial material using the carbodiimide chemistry. Alternately, the functionalized PEA can be coated onto a medical device, and the biobeneficial material can then be grafted onto the coating using the carbodiimide chemistry.

Derivatization via Multifunctional Aziridine

In accordance with a further aspect of the present invention, a multifunctional aziridine agent can be used as a crosslinker to couple the PEA polymer with a biobeneficial material having carboxylic acid groups. For example, pentaerythritol tris(3-aziridinopropionate) from Sybron Chemicals (NJ) can be used as a crosslinker (see, for example, Gianolino, D. A., et al., Crosslinked sodium hyaluronate containing labile linkages, Abstract from Society for Biomaterials 2002) (Scheme 4).

Scheme 4

In the derivatized PEA shown in Scheme, some residual aziridine groups will still be available at the surface to graft PEA and a biobeneficial material with carboxyl functionality.

Derivatization with a Multifunctional Carbodiimide

In another aspect of the present invention, a multifunctional carbodiimide can be used to attach the PEA polymer to a biobeneficial material with carboxylic acid functionalities (see Scheme 5). Multifunctional carbodiimides are available from Nisshinbo (CARBODILITE™) and Bayer (BAYDERM™ Fix CD).

Scheme 5

The PEA crosslinked according to Scheme 5 can have unreacted carbodiimide groups, and thus can be readily coupled to a biobeneficial material.

Derivatization by Coupling to a Biobeneficial Material with Primary Amine Functional Groups In accordance with a further aspect of the present invention, the PEA polymer can be attached to a biobeneficial material bearing primary amine functionalities via direct EDC mediated amide formation between the amine groups and the carboxyls of the PEA polymer. For example, monomers having primary amine functional functionality such as N-(3-aminopropyl)methacrylamide HCl (available from Polysciences), ethyl 3-aminocrotonate (available from Aldrich), ethyl 3-amino-4,4,4-trifluorocrotonate (available from Aldrich), or combinations thereof can undergo polymerization reaction to form a polymer bearing pendant primary amine groups. The primary amine groups can react with a biobeneficial moiety such as succinimidyl poly(ethylene glycol) (PEG) and the PEA polymer with carboxyl groups to form a D-PEA with a biobeneficial moiety.

Derivatization of PEA via the Amino Group of the PEA Polymer

In one embodiment, the amino active groups on the PEA polymer can be used to couple a biobeneficial material to the PEA polymer. In one embodiment, the active amino group on the PEA polymer can be attached to a biobeneficial material by alkylation of the amino group, forming a quaternary amine (Scheme 6):

Scheme 6

X = I, Br, Cl
R = biobeneficial material

This reaction proceeds best when the carbon atom bearing the leaving group is primary or secondary.

In another embodiment, the PEA polymer can be derivatized via the formation of an amide group by reaction of the amino group with an acid chloride, or other halogenated acid (Scheme 7):

Scheme 7

X = I, Br, Cl
R = biobeneficial material

The active amino group can be subjected to reductive amination with an aldehyde in a biobeneficial material in the presence of a reducing agent, e.g., NaCNBH$_3$ and NaBH$_4$ (Scheme 8) so as to attach a PEA polymer to a biobeneficial material:

Scheme 8

R = biobeneficial material

Alternatively, an amino group on the PEA polymer can react with an anhydride, an epoxide, isocyanate, or isothiocyanate respectively on a biobeneficial material so as to form a derivatized PEA (Scheme 9):

Scheme 9

In Scheme 9, R is a biobeneficial material.

Derivatization of PEA with Fullerenes

Fullerenes are compounds formed of pure carbon atoms whose molecular structure is characterized by alternating carbon-carbon double bonds that form interconnected and fused aromatic rings forming a closed structure. One such fullerenes is C60, which is commonly called "buckyball." It has been fully documented that fullerenes can be derivatized and functionalized. See, for example, Fullerenes: Chemistry, Physics, and Technology, Karl M. Kadish (Editor), Rodney S. Ruoff (Editor). For example, fullerenes can be functionalized to attach functional groups such as halides, carboxylic groups, keto, amino, ester, hydroxyl, and other functional groups to the molecule. See, e.g., Yang, et al., "Design and synthesis of fullerene-based amino acids," Abstract, 228th ACS National Conference, Philadelphia, Aug. 22-26, 2004, for attaching amino acids to fullerenes, Diederich, F., Pure & Appl. Chem., 69:395-400 (1997), for functionalizing fullerenes with acetylene, silanes, esters, and hydroxyl groups. Note, these functional groups would allow further derivatization or functionalization of fullerene by standard organic methodology such as catalytic hydration, reduction, oxidization, derivatization with halides, and/or hydrolysis. See, for example, Fullerenes: Chemistry, Physics, and Technology, Karl M. Kadish (Editor), Rodney S. Ruoff (Editor).

The functionalized fullerenes can be attached to a PEA polymer per the methods described above.

Bioactive Agents

The D-PEA polymer described herein can form a coating or a medical device such as a stent with one or more bioactive agents. These bioactive agents can be any agent, which is a therapeutic, prophylactic, or diagnostic agent. These agents can have anti-proliferative or anti-inflammatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysacchamides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and-its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIbb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or codrugs thereof. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent required can depend upon factors such as the particular circumstances of the patient; the nature of the tissues being delivered to; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Coating Construct

In another aspect of the present invention, the D-PEA can be used to form coatings that provide for controlled release of drugs. The D-PEA can be used alone or in combination with a biocompatible, non-bioabsorbable polymer or with a biocompatible, bioabsorbable polymer described above to form a controlled release matrix with a drug. This matrix can be coated onto a medical device such as a stent to form a drug reservoir layer of coating. In one embodiment, the D-PEA, optionally with a biobeneficial material and/or a biocompatible polymer, can also be top coated onto the drug reservoir layer to provide a controlled release of the drug.

In some embodiments, the controlled drug release coating construct includes a layer of coating that includes drug matrix which can be a bioabsorbable. A layer of coating that includes a D-PEA described above, optionally with a biobeneficial material (e.g., PolyActive™) and/or a biocompatible polymer, can be coated beneath and/or on top of the drug matrix layer to provide a controlled release of the drug.

In some embodiments, the controlled drug release coating construct includes a drug matrix containing a drug and a bioabsorbable polymer, a layer of a bioabsorbable polymer which is not D-PEA coated beneath the drug matrix, and a layer of D-PEA coated on top of the drug matrix to provide a controlled release of the drug.

In some other embodiments, the drug matrix can contain a non-degradable polymer and a drug. A layer of a D-PEA or a mixture of D-PEAs can be coated on top of the drug matrix to provide controlled release of the drug. Any non-degradable, biocompatible polymer can be used to form this coating construct. In one embodiment, the non-degradable, biocompatible polymer is Solef™ polymer described above. The D-PEA can be any derivatized PEA, one example of which is PEA-PEG.

In some further embodiments, the D-PEA can be used to modify the drug release rate of a PolyActive™ coating. For example, the D-PEA can be coated onto a medical device together with PolyActive™, optionally with a drug. A layer of pure PolyActive™ can then be coated on top of the layer of D-PEA/PolyActive™, which optionally includes a drug.

Examples of Implantable Devices

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design, for example, metallic stents with channels, pores, perforations or depots. The device can be made of a metallic material or an alloy such as, but not limited to, cobalt chromium alloy (ELGILOY), stainless steel (31 6L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Method of Use

In accordance with embodiments of the invention, a coating of the various described embodiments can be formed on an implantable device or prosthesis, e.g., a stent. For coatings including one or more active agents, the agent will retain on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachealbronchi and other biological passageways. A stent having the above-described coating is particularly useful for treating occluded regions of blood vessels caused by atherosclerosis, abnormal or inappropriate migration and proliferation of smooth muscle cells, thrombosis, and restenosis. Stents may be placed in a wide array of blood vessels, both arteries and veins. Representative examples of sites include the iliac, renal, carotid, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment.

Over the guidewire is passed a delivery catheter, which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth examples. All parameters and data are not to be construed to unduly limit the scope of the embodiments of the invention.

Example 1

Derivatized Poly (Ester Amide)/Everolimus Reservoir with Derivatized PEA Topcoat 12 mm small Vision™ stents (available from Guidant Corporation) were coated with 550 µg of a D-PEA/everolimus blend at a drug/polymer ratio of ¼ (w/w), the D-PEA being PEA derivatized with 4-amino-TEMPO. A solution of 2% (w/w) D-PEA and 0.5% everolimus in 200 proof ethanol was applied to the stent by spray and baked at 50° C. for one hour to remove the solvent. A topcoat of pure D-PEA was applied as a 2% (w/w) solution in ethanol by spraying until 290 µg of dry polymer solids was placed onto the stent followed by baking at 50° C. for one hour. The stents were sterilized by electron beam radiation in an argon atmosphere at a dose of 25 KGy.

Example 2

PEA/Everolimus Reservoir with A PEA Rate Release Limiting Topcoat and a D-PEA Biobeneficial Coat 12 mm small Vision™ stents (available from Guidant Corporation) were coated with 430 µg of a poly(ester amide)/everolimus blend at a drug/polymer ratio of 3 (w/w). A solution of 2% (w/w) poly(ester amide) polymer and 0.67% everolimus in 200 proof ethanol was applied to the stent by spray and baked at 50° C. for one hour to remove the solvent. A topcoat of a pure poly(ester amide) was applied as a 2% (w/w) solution in ethanol by spraying until 310 µg of dry polymer solids was placed onto the stent followed by baking at 50° C. for one hour. A biobeneficial coat of a PEA derivatized with 4-amino-TEMPO was coated from a 2% solution in 200 proof ethanol. 100 µg of dry solids was applied by spraying and baked at 50° C. for one hour. The stents were sterilized by electron beam radiation in an argon atmosphere at a dose of 25 KGy.

Example 3

Derivatized Poly (Ester Amide)/Everolimus Reservoir with Derivatized PEA Topcoat A 2%(w/w) solution of poly(n-butyl methacrylate) in a solvent blend of 50/50 (w/w) acetone/cyclohexanone was applied by spray to an 18 mm small Vision™ stent (available from Guidant Corporation). After 80 µg of polymer was accumulated, the stents were baked at 80° C. for 30 minutes. A drug/polymer reservoir layer was formed by spraying 812 µg of everolimus/poly(vinylidene fluoride-co-hexafluoropropene) (Solef 21508) D/P1/3.115 (w/w) in a solvent blend of acetone/cyclohexanone 70/30 (w/w). After coating was placed onto the stent it was baked at 50° C. for one hour. Onto this was placed 90 µg of a PEA derivatized with 4-amino-TEMPO to serve as a biobeneficial topcoat. This was applied by spray from a 2% solids solution (w/w) in a solvent blend of 90/10 ethanol/DMAC and baked at 50° C. for one hour.

For the coatings formed in Examples 1-3, the total drug content was determined by extracting the stents in acetonitrile followed by analysis of the extract by HPLC. The results are shown in Table 1.

TABLE 1

| Total Drug Content | | |
|---|---|---|
| System | Total Drug Content % Non-Sterile | Total Drug Content %, Sterile |
| Example 1. D-PEA on D-PEA/everolimus matrix | 99 ± 1 | 97 ± 0.7 |
| Example 2. D-PEA on PEA with PEA/everolimus matrix | 98 ± 1 | 93 ± 0.7 |
| Example 3. D-PEA on PVDF-HFP, 190 µg/cm² dose | 90 ± 0.3 | 84 ± 1.3 |

The purity of the everolimus on the stent was determined by an HPLC method that differs from the HPLC method for total content in that it is a gradient method versus isocratic, the run time is longer, and the concentration of injected drug is higher in order to quantify the small degradation peaks. Table 2 shows the results of analysis of peak purity for the three types of systems.

TABLE 2

| Analysis of Peak Purity of D-PEA Coatings | | |
|---|---|---|
| System | Peak Purity %6-Isomer | %7-Isomer |
| Example 1. D-PEA on D-PEA/everolimus, non-sterile n = 3 | 94.0 ± 2 | 4.6 ± 1.3 |
| Example 1. D-PEA on D-PEA/everolimus, E-beam n = 3 | 94.5 ± 0.3 | 4.1 ± 0.01 |
| Example 2. D-PEA on PEA, non-sterile n = 3 | 97.1 ± 0.3 | 1.5 ± 0 |
| Example 2. D-PEA on PEA, E-beam n = 3 | 97.0 ± 0.3 | 1.5 ± 0.006 |
| PVDF-HFP/PBMA 190 dose E-beam (Typical) | 96 | 2 |

Figure 1:
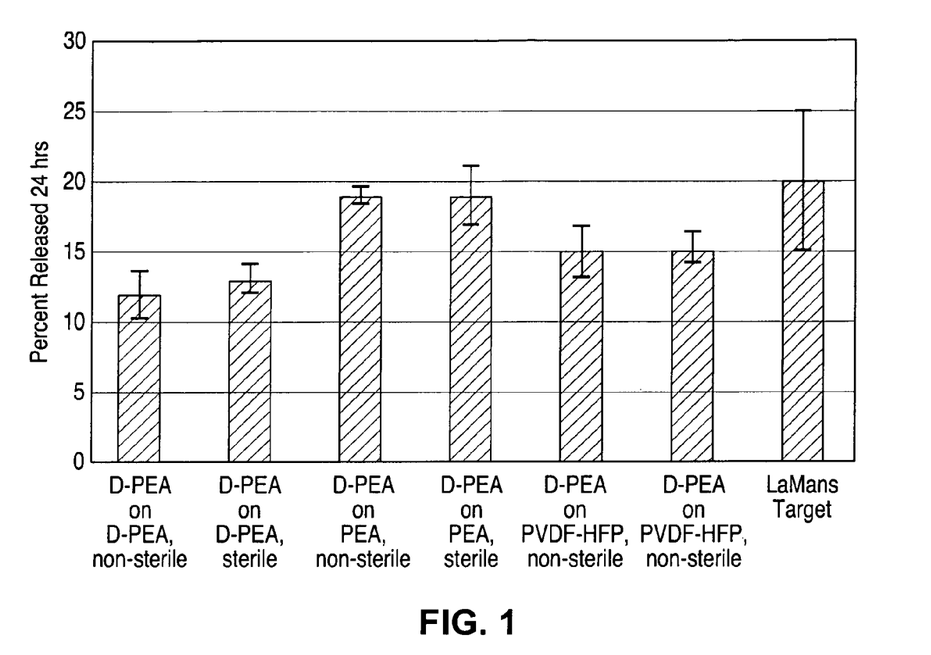
FIG. 1 shows the in vitro release of DES coatings containing a derivatized poly(ester amide) polymer.
Figure 2:
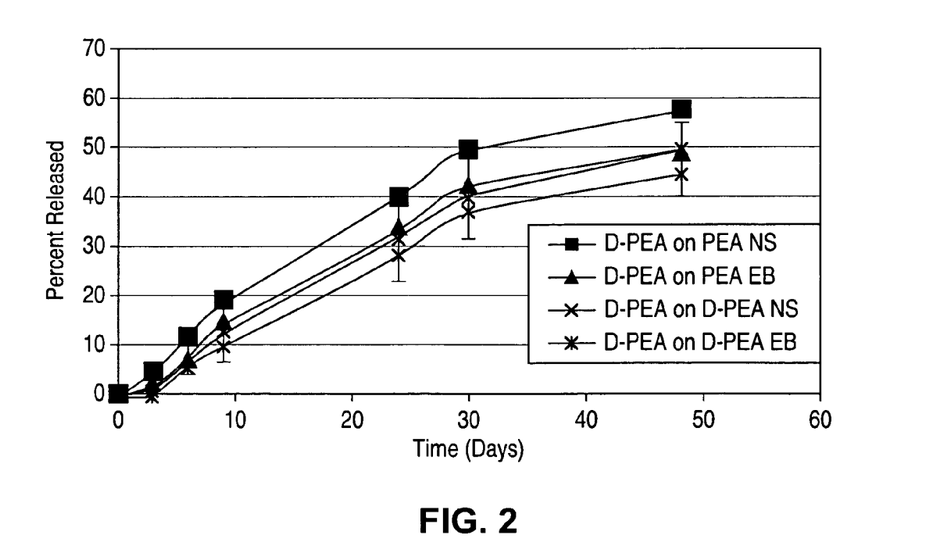
FIG. 2 shows cumulative percent of in-vitro released everolimus from coatings containing a poly(ester amide) polymer (In-Vitro Triton X-100)

The in-vitro release rate was measured in porcine serum by incubating the stens in porcine serum for 24 hours at 37° C. and then assaying the amount of drug left on the stent (FIG. 1). The in vitro release of these systems in a solution of 1% triton x-100 at 37° C. is shown in FIG. 2. These data demonstrate that systems composed of a derivatized PEA topcoated on derivatized PEA reservoirs, D-PEA topcoated on PEA reservoirs, or D-PEA topcoated on PVDF-HFP drug reservoirs can control the release of everolimus in two in-vitro models. E-beam sterilization at 25 KGy slows the drug release rates slightly and results in only a small loss of drug content.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating on a medical device comprising a layer comprising a derivatized poly(ester amide)(D-PEA),
the D-PEA being derivatized with a biobeneficial moiety selected from the group consisting of poly(vinyl pyrrolidone), poly(styrene sulfonate), poly(hydroxypropyl methacrylamide), hyaluronic acid, fibrin, albumin, elastin, dextran, and combinations thereof;
wherein the D-PEA is further derivatized with a nitric oxide preserver moiety.

2. The coating of claim 1, wherein the biobeneficial moiety is poly(vinyl pyrrolidone).

3. The coating of claim 1, wherein the biobeneficial moiety is poly(styrene sulfonate).

4. The coating of claim 1, further comprising a bioactive agent.

5. The coating of claim 4, wherein the bioactive agent is selected from the group consisting of paclitaxel, docetaxel, estradiol, nitric oxide donors, super oxide dismutases, 4-amino-2,2,6,6-tetramethylpiperidine-1-oxyl (4-amino-TEMPO), tacrolimus, dexamethasone, rapamycin, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, ABT-578, clobetasol, progenitor cell capturing antibody, and combinations thereof.

6. The coating of claim 1, wherein the layer of D-PEA is coated on top of a drug matrix.

7. The coating of claim 6, wherein the drug matrix comprises a D-PEA.

8. The coating of claim 1, wherein the medical device is a stent.

9. The coating of claim 6, wherein the medical device is a stent.

10. The coating of claim 6, wherein the medical device is a metallic stent with channels, pores, perforations and/or depots.

11. The coating of claim 6, wherein the medical device is a metallic stent formed of a material comprising magnesium, stainless steel, cobalt-chromium alloy or nitinol.

12. A medical device formed of a material comprising a derivatized poly(ester amide) (D-PEA),
the D-PEA being derivatized with a biobeneficial moiety selected from the group consisting of poly(vinyl pyrrolidone), poly(styrene sulfonate), poly(hydroxypropyl methacrylamide), hyaluronic acid, fibrin, albumin, elastin, dextran, and combinations thereof;
where the D-PEA is further derivatized with a nitric oxide preserver moiety.

13. The medical device of claim 12, wherein the D-PEA is included in a coating layer for the device.

14. The medical device of claim 12, wherein the biobeneficial moiety is poly(vinyl pyrrolidone).

15. The medical device of claim 12, further comprising a bioactive agent.

16. The medical device of claim 12 which is a stent.

17. A stent comprising a coating according to claim 1.

18. The coating of claim 1, wherein the biobeneficial moiety is poly(hydroxypropyl methacrylamide).

19. The coating of claim 1, wherein the biobeneficial moiety is hyaluronic acid.

20. The coating of claim 1, wherein the biobeneficial moiety is fibrin.

21. The coating of claim 1, wherein the biobeneficial moiety is albumin.

22. The coating of claim 1, wherein the biobeneficial moiety is elastin.

23. The coating of claim 1, wherein the biobeneficial moiety is dextran.

* * * * *